US011602845B2

(12) United States Patent
Rubæk et al.

(10) Patent No.: US 11,602,845 B2
(45) Date of Patent: Mar. 14, 2023

(54) METHOD OF DETECTING HUMAN AND/OR ANIMAL MOTION AND PERFORMING MOBILE DISINFECTION

(71) Applicant: UVD Robots Aps, Odense (DK)

(72) Inventors: Thomas Rubæk, Odense (DK); Efraim Vitzrabin, Odense (DK); John Erland Østergaard, Odense (DK); Rune Larsen, Odense (DK); Jorge Rodriguez, Copenhagen (DK); Simon Elison, Langeskov (DK)

(73) Assignee: UVD Robots ApS, Odense (DK)

( * ) Notice: Subject to any disclaimer, the term of this patent is extended or adjusted under 35 U.S.C. 154(b) by 244 days.

(21) Appl. No.: 16/889,434

(22) Filed: Jun. 1, 2020

(65) Prior Publication Data

US 2021/0370505 A1     Dec. 2, 2021

(51) Int. Cl.
    *B25J 9/16*      (2006.01)
    *B25J 11/00*     (2006.01)
    (Continued)

(52) U.S. Cl.
    CPC ............. *B25J 9/1653* (2013.01); *B25J 9/161* (2013.01); *B25J 9/1664* (2013.01); *B25J 9/1679* (2013.01);
    (Continued)

(58) Field of Classification Search
    CPC .............................. B25J 9/1664; B25J 13/086
    See application file for complete search history.

(56) References Cited

U.S. PATENT DOCUMENTS

| 2015/0359915 A1 | 12/2015 | Farren |
| 2016/0136313 A1 | 5/2016 | Nguyen |

(Continued)

FOREIGN PATENT DOCUMENTS

| AU | 2018241204 B2 * | 5/2020 | ............... A61L 2/10 |
| CN | 107875413 A | 4/2018 | |

(Continued)

OTHER PUBLICATIONS

Partial European Search Report for App. No. EP20178366.9, dated Nov. 9, 2020, 12 pages.

(Continued)

*Primary Examiner* — Kevin Joyner
*Assistant Examiner* — Changru Chen
(74) *Attorney, Agent, or Firm* — Kevin Roddy; Butzel Long

(57) ABSTRACT

Implementations of the disclosed subject matter provide a method of moving a mobile robot within an area. The movement of the mobile robot and the emission of ultraviolet (UV) light may be stopped when a human and/or animal is determined to be within the area. Using at least one sensor, the method may be determine whether there is at least one of human identification, animal identification, motion, heat, and/or sound within the area for a predetermined period of time. When there is no human identification, animal identification, motion, heat, and/or sound within the predetermined period of time, UV light may be emitted and the drive system may be controlled to move the mobile robot within the area. When there is at least one of human identification, motion, heat, and/or sound within the predetermined period of time, a light source may be controlled to prohibit the emission of UV light.

8 Claims, 11 Drawing Sheets

(51) Int. Cl.
    *B25J 13/08*     (2006.01)
    *B25J 19/06*     (2006.01)
    *B25J 5/00*     (2006.01)
    *B25J 19/04*     (2006.01)
    *A61L 2/10*     (2006.01)

(52) U.S. Cl.
CPC ......... *B25J 11/0085* (2013.01); *B25J 13/086* (2013.01); *B25J 13/087* (2013.01); *B25J 19/04* (2013.01); *B25J 19/061* (2013.01); *A61L 2/10* (2013.01); *A61L 2202/11* (2013.01); *A61L 2202/16* (2013.01); *B25J 5/007* (2013.01)

(56) References Cited

U.S. PATENT DOCUMENTS

| | | |
|---|---|---|
| 2016/0151521 A1 | 6/2016 | Nathan |
| 2016/0271803 A1 | 9/2016 | Stewart |
| 2016/0296649 A1 | 10/2016 | Ramanand |
| 2017/0157276 A1 | 6/2017 | Dobrinsky |
| 2017/0224853 A1 | 8/2017 | Jay |
| 2017/0296686 A1 | 10/2017 | Cole |
| 2018/0117194 A1 | 5/2018 | Dobrinsky |

FOREIGN PATENT DOCUMENTS

| | | | |
|---|---|---|---|
| CN | 109414519 A | 3/2019 | |
| CN | 208705724 U | 4/2019 | |
| CN | 209048710 U | 7/2019 | |
| CN | 111150862 A | 5/2020 | |
| KR | 101742489 B1 * | 6/2017 | ............... A61L 2/24 |
| TW | 487799 B | 5/2002 | |

OTHER PUBLICATIONS

Extended European Search Report for App. No. EP20178366.9, dated Feb. 9, 2021, 10 pages.
Taiwanese Search Report (with English translation) for App. No. TW109118821, dated Dec. 2, 2021, 2 pages.
Summons to Attend Oral Proceedings issued in App. No. EP20178366, dated Aug. 8, 2022, 10 pages.
Chinese Office Action issued in App. No. CN202010546187, dated Sep. 22, 2022, 8 pages.

* cited by examiner

US 11,602,845 B2

METHOD OF DETECTING HUMAN AND/OR ANIMAL MOTION AND PERFORMING MOBILE DISINFECTION

BACKGROUND

Mobile devices, such as mobile robots, can be operated so as to disinfect indoor areas, such as a room that has surfaces contaminated with bacteria, viruses, or other pathogens. When such robots are remotely operated, it is difficult for the remote operator to determine when a person enters an area that is being disinfected. Similarly, when such robots are autonomously operated, it is difficult for the robot to determine when a person enters an area that is being disinfected. Some disinfection modalities can be harmful to humans and/or animals.

BRIEF SUMMARY

According to an implementation of the disclosed subject matter, a method may be provided that includes moving, using a drive system, a mobile robot within an area, and emitting, using a light source of the mobile robot, ultraviolet (UV) light to disinfect at least a portion of the area. While emitting the UV light, the method may determine whether there is a human and/or an animal within the area using at least one sensor. The movement of the mobile robot within the area may be stopped by controlling the drive system and stopping the emission of the UV light by controlling the UV light source when the human and/or animal is determined to be within the area. The method may include determining, using the at least one sensor, whether there is at least one of human and/or animal identification, motion, heat, and/or sound within the area for a predetermined period of time. When the at least one sensor determines that there is no human and/or animal identification, motion, heat, and sound within the predetermined period of time, the light source may be controlled to emit UV light and the drive system may be controlled to move the mobile robot within the area. When the at least one sensor determines that there is at least one of human and/or animal identification, motion, heat, and/or sound within the predetermined period of time, the light source may be controlled to prohibit the emission of UV light.

Additional features, advantages, and implementations of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

Figure 1:
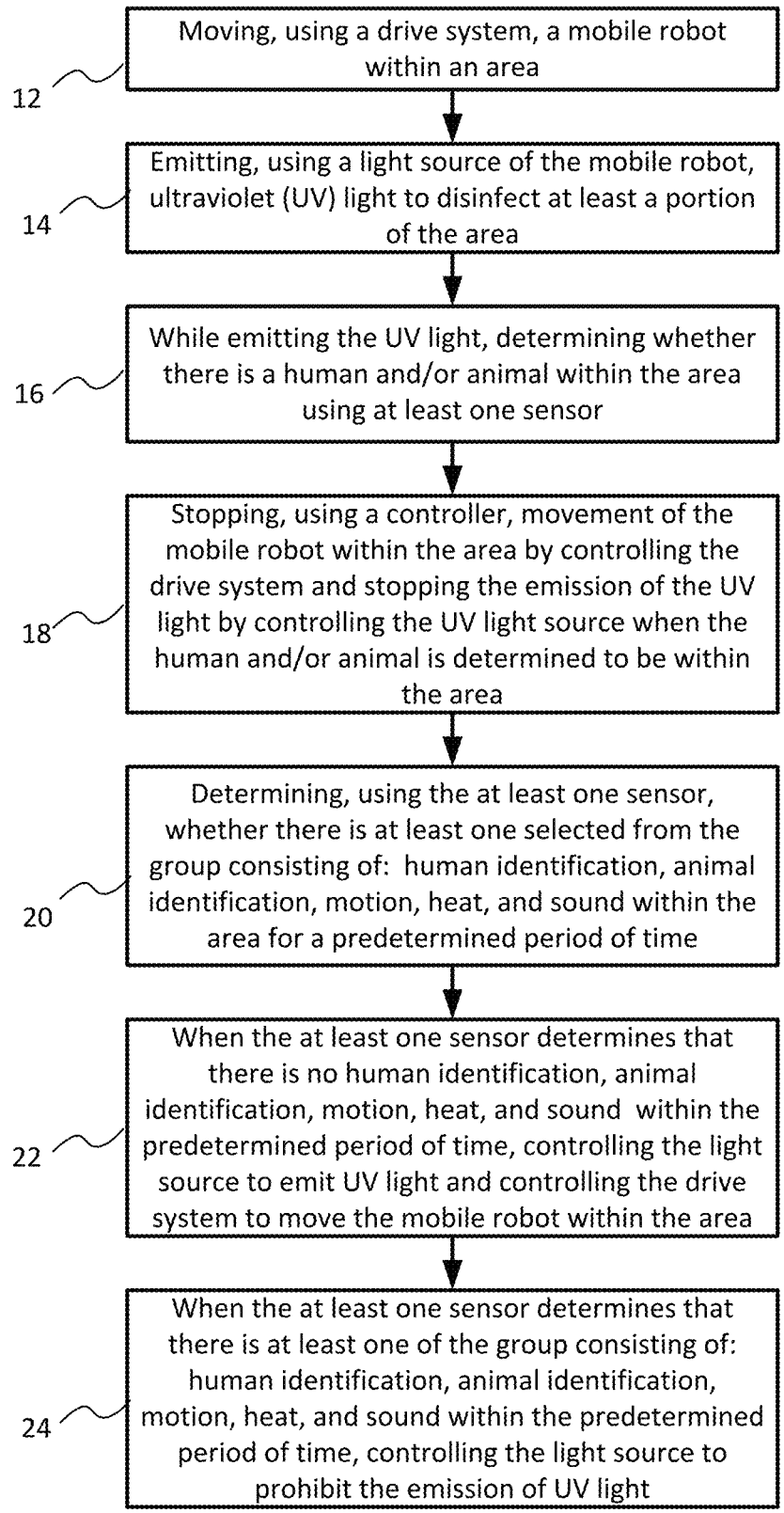
FIG. 1 shows an example method of controlling the movement of a mobile robot within a predetermined area, outputting ultraviolet (UV) light having a dosage level to disinfect the predetermined area, and stopping the output of UV light when a human and/or an animal is detected according to an implementation of the disclosed subject matter.

Implementations of the disclosed subject matter provide a mobile robot that may move about a predetermined area and output ultraviolet (UV) light to disinfect the predetermined area. The mobile robot may be used as part of a regular cleaning cycle of a room, building, airplane, school, or the like, and may prevent and/or reduce the spread of infectious diseases, viruses, bacteria, and other types of harmful organic microorganisms in the environment by breaking down their DNA-structure with UV light.

Implementations of the disclosed subject matter provide methods of controlling the operation of the mobile robot to protect humans and/or animals from the UV light output by the mobile robot. Sensors may be placed at the one or more entrances to an area to be disinfected. In hospitals and/or other buildings, there may be a need to disinfect large areas, which may have a plurality of entrances. Walls and other obstacles of the building and/or room may cause interference to the communication between the sensors disposed near an entrance to a room and a mobile robot. Implementations of the disclosed subject matter provide a mobile robot with one or more sensors that may be used to determine if a human and/or an animal is within an area being disinfected with UV light. For example, the one or more sensors may include an image sensor, RGB (red green blue) camera, thermal camera, geometrical sensors, a microphone, and the like.

In some implementations, the sensor (e.g., an RGB camera, an image sensor, or the like) may determine if a human and/or an animal is within the captured image. Once a human and/or an animal has been detected, the mobile robot may be controlled so as to stop its movement and to stop the output of UV light from the light source for a predetermined period of time so that the human and/or animal will not be harmed and that the mobile robot may more accurately determine if a human and/or an animal is present in the area. In some implementations, when the human and/or animal is detected, the mobile robot may be controlled to stop the output of UV light from the light source for a predetermined period of time, and may be controlled to move to a predetermined portion of the area. The mobile robot may provide an audio and/or visual alert for the stoppage. That is, while the mobile robot has stopped and is no longer outputting UV light, it may use the one or more sensors to determine whether a human and/or animal is present within the area.

If an object initially detected as human and/or animal is confirmed during the predetermined period of time to be "non-human" and/or "non-animal," the non-human and/or non-animal object may be identified on a map and stored in memory. That is, the next time that the same object is detected as a human and/or an animal in the same area of the map, it may not be triggered as a potential human and/or potential animal by the one or more sensors of the robot. In some implementations, this may be disabled to provide additional safety, so that each object detected as a potential human and/or potential may stop the operations of the robot so that the object may be confirmed as being human and/or animal, or not.

If a thermal camera is used by the mobile robot to initially determine whether a human and/or animal is within the room, there may be more false positives with this type of sensor. Stopping the mobile robot and the output of UV light may be important for human and/or animal safety. For example, hospital personnel may wear protective clothing, and the thermal camera may have difficulty detecting them as humans. In another example, light bulbs may be in the shape of human heads, and may lead to false positives. The mobile robot may stop and refrain from outputting UV light to determine whether the detected object is a human and/or an animal by using one or more sensors.

In implementations of the disclosed subject matter, the at least one sensor of the mobile robot may include geometric sensors, which may be used by the robot to determine its position within the area and/or on a map. When the mobile robot initially determines that an object may be a human and/or an animal, and no such object is on the map, the mobile robot may stop moving and outputting UV light, and may determine whether the object is a human and/or an animal or not over the predetermined period of time.

In implementations of the disclosed subject matter, the mobile robot may determine whether a human and/or an animal is within the area after an initial detection by stopping the movement of the mobile robot and the output of UV light, and using one or more sensors to determine whether a human and/or an animal is present in the area over a predetermined period of time. This may provide additional safety to humans and/or animals within the area while the mobile robot performs disinfection operations.

Figure 8:
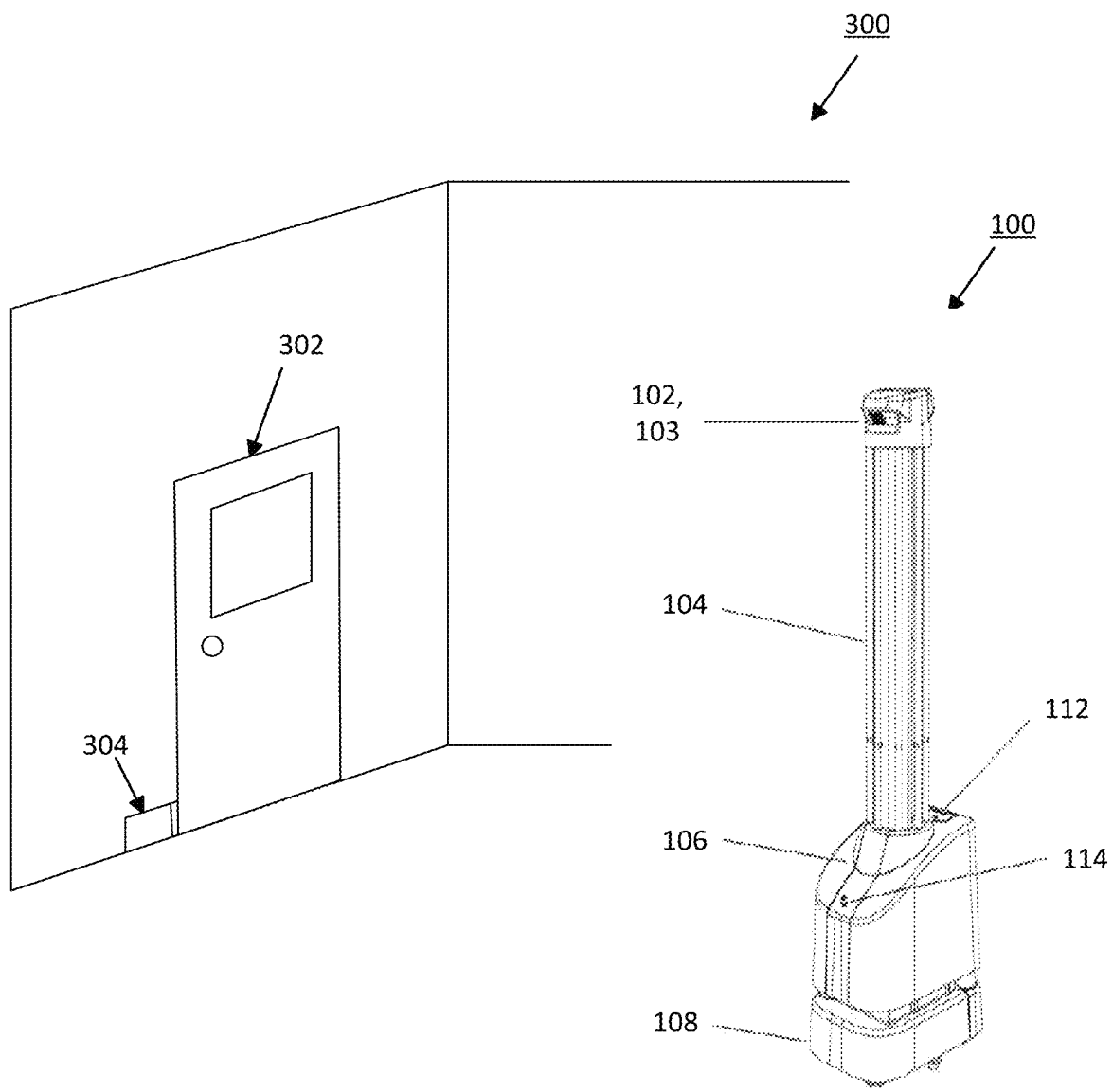
FIG. 8 shows a door sensor and a mobile robot having at least one sensor to monitor the opening of the door according to an implementation of the disclosed subject matter.
Figure 9:
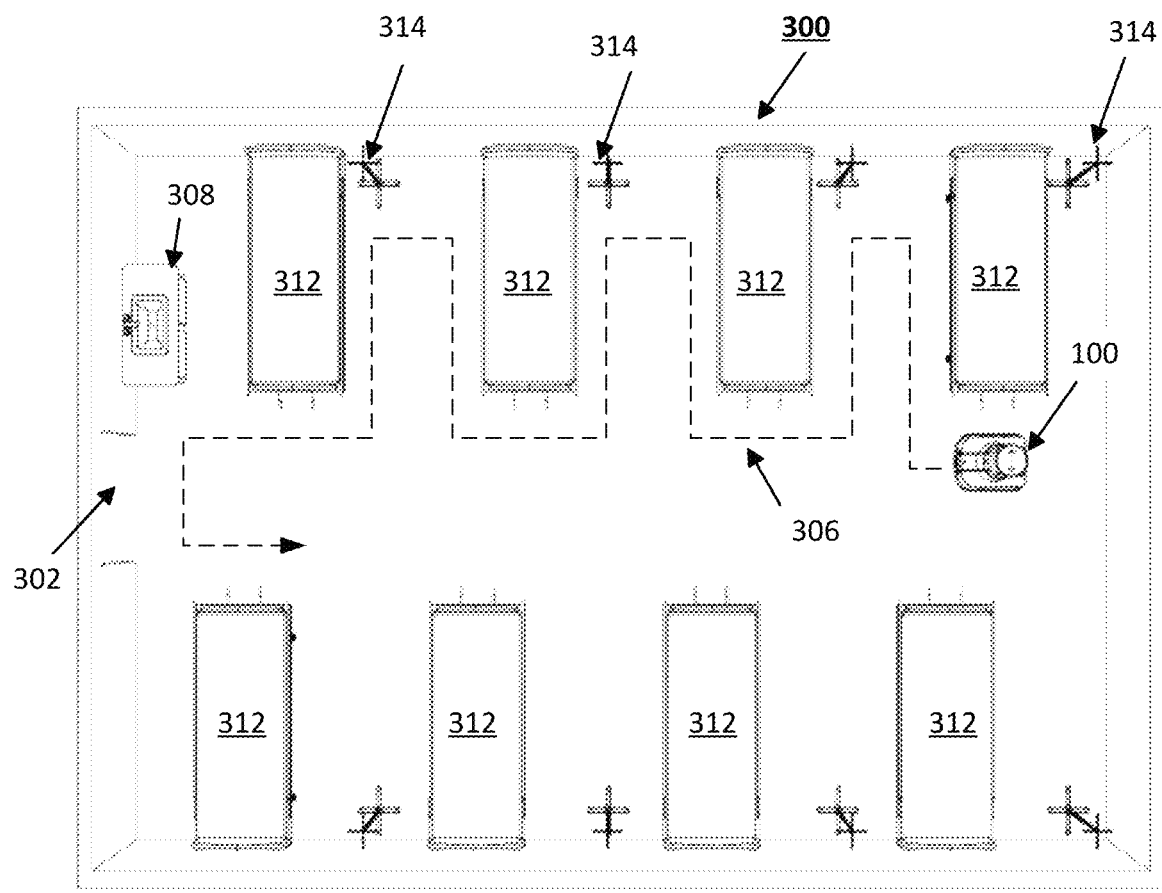
FIG. 9 shows an example of a path of the mobile robot to apply a dosage of UV light in an area and map non-human locations according to an implementation of the disclosed subject matter.

FIG. 1 shows an example method 10 of controlling the movement of a mobile robot within a predetermined area, outputting ultraviolet (UV) light having a dosage level to disinfect the predetermined area, and stopping the movement and outputting of UV light when a human and/or an animal is detected according to an implementation of the disclosed subject matter. At operation 12, a mobile robot (e.g., mobile robot 100 shown in FIGS. 4-6 and 8-11) may move within an area (e.g., 300 as shown in FIGS. 8-9) using a drive system (e.g. drive system 108 shown in FIG. 10). At operation 14, a light source (e.g., light source 104 shown in FIGS. 4, 6, 8, and 9 and described below) of the mobile robot may emit ultraviolet (UV) light to disinfect at least a portion of the area.

At operation 16, while emitting the UV light from the light source of the mobile robot, the controller (e.g., controller 114 shown in FIG. 10) and/or the at least one sensor may be used to determine whether there is a human and/or an animal within the area using at least one sensor (e.g., sensor 102 and/or sensor 106 and/or microphone 103 shown in shown in FIGS. 4-6, 8, and 10).

In some implementations, the determining whether the human and/or animal is within the area in operation 16 may include capturing an image, using at least one sensor, to determine whether the human and/or animal is within the area. For example, the sensor 102 and/or 106 of the mobile robot 100 that may capture the image. The sensor 102, 106 and/or the controller 114 may determine whether there is a human and/or an animal present within the captured image by using image and/or pattern recognition.

In some implementations, the determining whether the human and/or the animal is within the area in operation 16 may include capturing a thermal image by using a thermal sensor. The thermal sensor may be sensor 102 and/or 106 of the mobile robot 100. The sensor 102, 106 and/or the controller 114 may determine whether there is a human and/or an animal present within the captured thermal image by using, for example, pattern recognition.

At operation 18, the controller may stop the movement of the mobile robot within the area by controlling the drive system (e.g., drive system 108 shown in FIG. 10) and stopping the emission of the UV light by controlling the UV light source (e.g., light source 104 shown in FIGS. 4, 6, 8, and 9) when the human and/or the animal is determined to be within the area.

At operation 20, the at least one sensor may be used to determine whether there is at least one of human and/or animal identification, motion, heat, and/or sound within the area for a predetermined period of time. That is, the at least one sensor and/or the controller may be used to identify whether a human and/or an animal is present within a captured image, whether there is motion within the area which may indicate that a human and/or an animal is present based on the pattern of motion, whether a human and/or an animal is present within a thermal image based on emission profile of the image, and/or whether sound captured by the microphone indicates that a human and/or an animal is present within the area (e.g., detection of voice, animal noises, footsteps, breathing, or the like).

In implementations of the disclosed subject matter, a human and/or an animal may be detected by a thermal camera and/or infrared camera, which may be sensor 102, 106. For example, the mobile robot having the thermal camera and/or infrared camera may determine the heat of an object and/or one or more portions of the object within the view of the camera. If the heat is around 36° C., the mobile robot may determine that a human is suspected as appearing in the image captured by the camera. In some implementations, when a human and/or animal is located a predetermined distance or more from the camera, the heat information may be captured by one or more pixels of the camera.

Implementations of the disclosed subject matter provide a mobile robot that may move about a predetermined area and output ultraviolet (UV) light to disinfect the predetermined area. The mobile robot may be used as part of a regular cleaning cycle of a room, building, airplane, school, or the like, and may prevent and/or reduce the spread of infectious diseases, viruses, bacteria, and other types of harmful organic microorganisms in the environment by breaking down their DNA-structure with UV light.

Implementations of the disclosed subject matter provide methods of controlling the operation of the mobile robot to protect humans and/or animals from the UV light output by the mobile robot. Sensors may be placed at the one or more entrances to an area to be disinfected. In hospitals and/or other buildings, there may be a need to disinfect large areas, which may have a plurality of entrances. Walls and other obstacles of the building and/or room may cause interference to the communication between the sensors disposed near an entrance to a room and a mobile robot. Implementations of the disclosed subject matter provide a mobile robot with one or more sensors that may be used to determine if a human and/or an animal is within an area being disinfected with UV light. For example, the one or more sensors may include an image sensor, RGB (red green blue) camera, thermal camera, geometrical sensors, microphone, and the like.

In some implementations, the sensor (e.g., an RGB camera, an image sensor, or the like) may determine if a human and/or an animal is within the captured image. Once a human and/or an animal has been detected, the mobile robot may be controlled so as to stop its movement and to stop the output of UV light from the light source for a predetermined period of time so that the human and/or animal will not be harmed and that the mobile robot may more accurately determine if a human and/or an animal is present in the area. In some implementations, when the human and/or animal is detected, the mobile robot may be controlled to stop the output of UV light from the light source for a predetermined period of time, and may be controlled to move to a predetermined portion of the area. The mobile robot may provide an audio and/or visual alert for the stoppage. That is, while the mobile robot has stopped and is no longer outputting UV light, it may use the one or more sensors to determine whether a human and/or an animal is present within the area.

If an object initially detected as human and/or animal is confirmed during the predetermined period of time to be "non-human" or "non-animal," the non-human and/or non-animal object may be identified on a map and stored in memory. That is, the next time that the same object is detected as a human and/or an animal in the same area of the map, it may not be triggered as a potential human and/or potential animal by the one or more sensors of the robot. In some implementations, this may be disabled to provide additional safety, so that each object detected as a potential human and/or potential animal may stop the operations of the robot so that the object may be confirmed as being a human and/or animal, or not.

If a thermal camera is used by the mobile robot to initially determine whether a human and/or an animal is within the room, there may be more false positives with this type of sensor. Stopping the mobile robot and the output of UV light may be important for human and/or animal safety. For example, hospital personnel may wear protective clothing, and the thermal camera may have difficulty detecting them as humans and/or animals. In another example, light bulbs may be in the shape of human heads, and may lead to false positives. The mobile robot may stop and refrain from outputting UV light to determine whether the detected object is a human and/or an animal by using one or more sensors.

In implementations of the disclosed subject matter, the at least one sensor of the mobile robot may include geometric sensors, which may be used by the robot to determine its position within the area and/or on a map. When the mobile robot initially determines that an object may be a human and/or an animal, and no such object is on the map, the mobile robot may stop moving and outputting UV light, and may determine whether the object is a human and/or animal or not over the predetermined period of time.

In implementations of the disclosed subject matter, the mobile robot may determine whether a human and/or animal is within the area after an initial detection by stopping the movement of the mobile robot and the output of UV light, and using one or more sensors to determine whether a human and/or an animal is present in the area over a predetermined period of time. This may provide additional safety to humans and/or animals within the area while the mobile robot performs disinfection operations.

FIG. 1 shows an example method 10 of controlling the movement of a mobile robot within a predetermined area, outputting ultraviolet (UV) light having a dosage level to disinfect the predetermined area, and stopping the movement and outputting of UV light when a human and/or an animal is detected according to an implementation of the disclosed subject matter. At operation 12, a mobile robot (e.g., mobile robot 100 shown in FIGS. 4-6 and 8-11) may move within an area (e.g., 300 as shown in FIGS. 8-9) using a drive system (e.g. drive system 108 shown in FIG. 10). At operation 14, a light source (e.g., light source 104 shown in FIGS. 4, 6, 8, and 9 and described below) of the mobile robot may emit ultraviolet (UV) light to disinfect at least a portion of the area.

Figure 10:
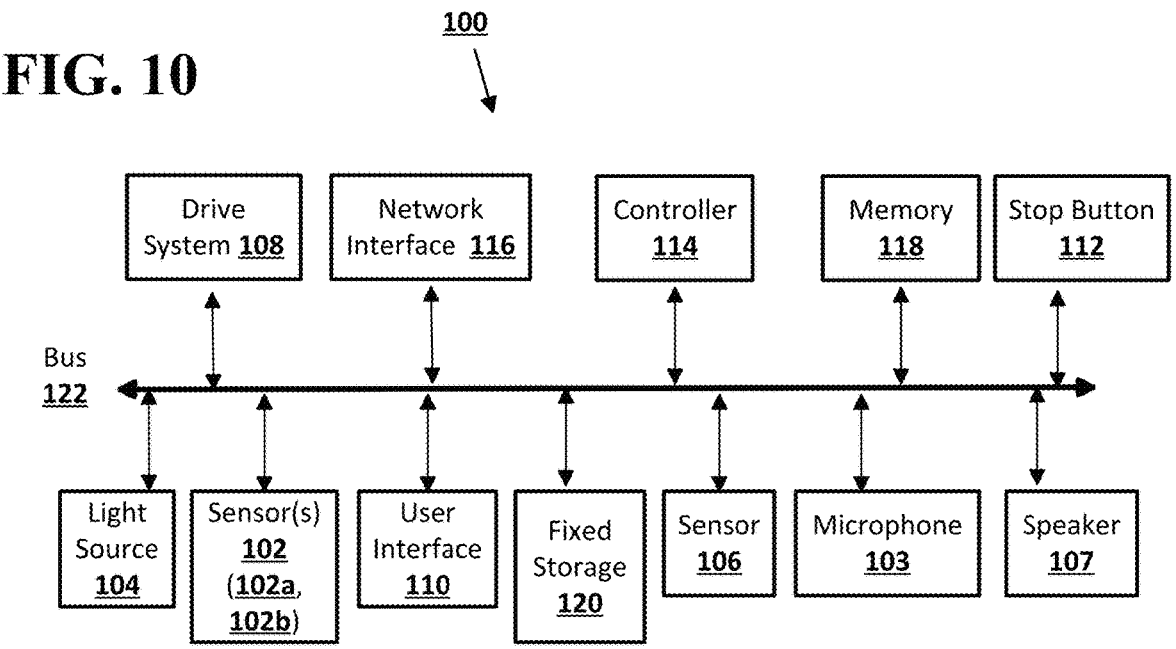
FIG. 10 shows an example configuration of the mobile robot of FIGS. 4-6 according to an implementation of the disclosed subject matter.

At operation 16, while emitting the UV light from the light source of the mobile robot, the controller (e.g., controller 114 shown in FIG. 10) and/or the at least one sensor may be used to determine whether there is a human and/or an animal within the area using at least one sensor (e.g., sensor 102 and/or sensor 106 shown in FIGS. 4-6 and 8, and/or microphone 109 shown in FIG. 10, which may be one of the sensors).

In some implementations, the determining whether the human and/or animal is within the area in operation 16 may include capturing an image (e.g., image 252, 258, 266 shown in FIGS. 7A-7C and described below) using at least one sensor, to determine whether the human and/or animal is within the area. For example, the sensor 102 and/or 106 of the mobile robot 100 that may capture the image. The sensor 102, 106, the controller 114, the server 140, and/or the remote platform 160 may determine whether there is a human and/or an animal present within the captured image by using image and/or pattern recognition.

In some implementations, the determining whether the human and/or animal is within the area in operation 16 may include capturing a thermal image (e.g., image 250, 256, 264 shown in FIGS. 7A-7C and described below) by using a thermal sensor. The thermal sensor may be sensor 102 and/or 106 of the mobile robot 100. The sensor 102, 106, the controller 114, the server 140, and/or the remote platform 160 may determine whether there is a human and/or an animal present within the captured thermal image by using, for example, pattern recognition.

At operation 18, the controller may stop the movement of the mobile robot within the area by controlling the drive system (e.g., drive system 108 shown in FIG. 10) and stopping the emission of the UV light by controlling the UV light source (e.g., light source 104 shown in FIGS. 4, 6, 8, and 9) when the human and/or animal is determined to be within the area. In some implementations, when the mobile robot 100 is being remotely operated (e.g., from commands received from the server 140 and/or remote platform 160 shown in FIG. 11), the remote operator may stop the movement of the mobile robot and/or operation of the UV light source when the remote operator determines that a human and/or animal is within the area. In some implementations, the controller may stop the movement of the mobile robot and/or the emission of UV light from the UV light source when a voice command is received by the mobile robot via a microphone (e.g., microphone 103 shown in FIG. 10). In some implementations, the controller may stop the movement of the mobile robot and/or the emission of UV light from the UV light source when stop button 112 (shown in FIG. 4) is selected.

At operation 20, the at least one sensor may be used to determine whether there is at least one of human and/or animal identification, motion, heat, and/or sound within the area for a predetermined period of time. That is, the at least one sensor and/or the controller may be used to identify whether a human and/or an animal is present within a captured image, whether there is motion within the area which may indicate that a human and/or an animal is present based on the pattern of motion, whether a human and/or an animal is present within a thermal image based on emission profile of the image, and/or whether sound captured by the microphone indicates that a human and/or an animal is present within the area (e.g., detection of voice, animal noises, footsteps, breathing, or the like).

At operation 22, when the at least one sensor determines that there is no human and/or animal identification, motion, heat, and/or sound within the predetermined period of time, the light source may be controlled to emit UV light and the drive system to move the mobile robot within the area. For example, the controller 114 shown in FIG. 10 may control the light source 104 and/or the drive system 108 of the mobile robot to move about path 306 in area 300 shown in FIG. 9 to disinfect the area, including beds 312, sink 308, 4-hook IV stands 314, and the like while there are no humans and/or animals present in the area.

Figure 11:
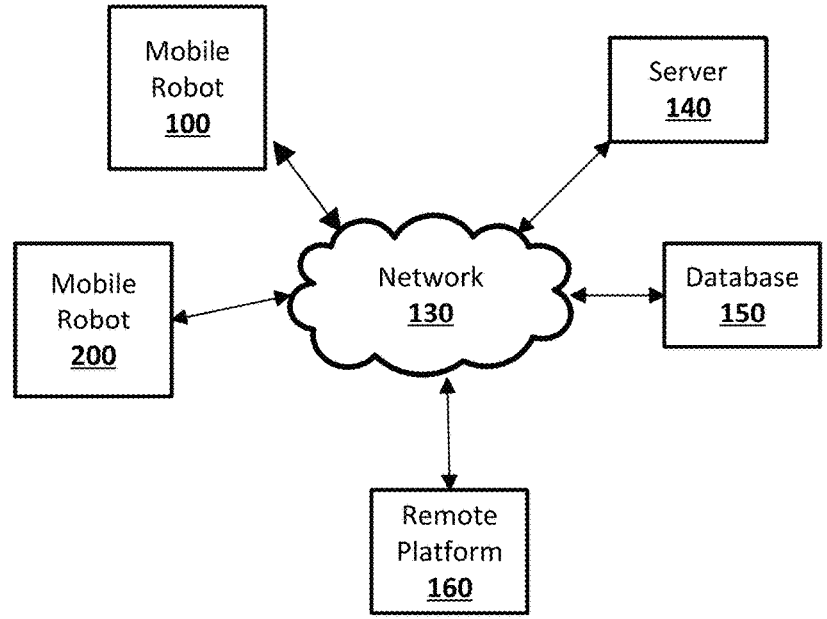
FIG. 11 shows a network configuration which may include a plurality of mobile robots according to implementations of the disclosed subject matter.

In some implementations, when the mobile robot 100 is being remotely operated (e.g., from commands received from the server 140 and/or remote platform 160 shown in FIG. 11), the remote operator may control the movement of the mobile robot and/or the operation of the UV light source when the remote operator determines that a human and/or animal is not within the area.

At operation 24, when the at least one sensor determines that there is at least one of human and/or animal identification, motion, heat, and/or sound within the predetermined period of time, the light source may be controlled to prohibit the emission of UV light. For example, the controller 114 shown in FIG. 10 may control the light source 104 to prohibit the emission of UV light. In some implementations, the controller may prohibit the movement of the mobile robot and/or the emission of UV light from the UV light source when a voice command is received by the mobile robot via a microphone (e.g., microphone 103 shown in FIG. 10). In some implementations, the controller may prohibit the movement of the mobile robot and/or the emission of UV light from the UV light source when stop button 112 (shown in FIG. 4) is selected.

In some implementations, a notification may be output that the human and/or animal is determined to be in the area, the movement of the mobile robot is being stopped, and/or the emission of the UV light from the light source is stopped. The output notification may be an audible notification and/or a visual notification. For example, the speaker 107 (shown in FIG. 10) of the mobile robot 100 may output the audible notification that the human and/or animal is determined to be in the area, the movement of the mobile robot is being stopped, and/or the emission of the UV light from the light source is stopped. The user interface 110 (shown in FIG. 10) of the mobile robot 100 may include a display to display the visual notification that the human and/or animal is determined to be in the area, the movement of the mobile robot is being stopped, and/or the emission of the UV light from the light source is stopped.

In some implementations, the notification may be transmitted using a communications interface of the mobile robot via a communications network. For example, the notification may be transmitted using the network interface 116 (shown in FIG. 10) of the mobile robot 100 via the network 130 to the server 140, database 150, and/or remote platform 160 shown in FIG. 11.

In some implementations, the location of the detected human as a non-human and/or the detected animal as non-animal on a map of the area in a memory that is communicatively coupled to the controller based on a signal received by a communications interface of the mobile robot via a communications network or an input received from an interface of the mobile robot. For example, operation 16 may determine that there is a human present in the area, but operation 20 may determine that there is no human (i.e., the object originally detected is human is non-human) in the area based on the lack of a human identification, motion detection, the heat, and/or sound signals generated by the at least one sensor. The location of the non-human and/or non-animal in the area may be stored in the fixed storage 120 (shown in FIG. 10) and/or the memory 118 of the mobile robot 100, and/or at the server 140, database 150, and/or remote platform 160 as shown in FIG. 11. The location of the non-human and/or non-animal may be determined by at least one of the sensor 102 and/or 106 of the mobile robot 100.

Figure 7A:
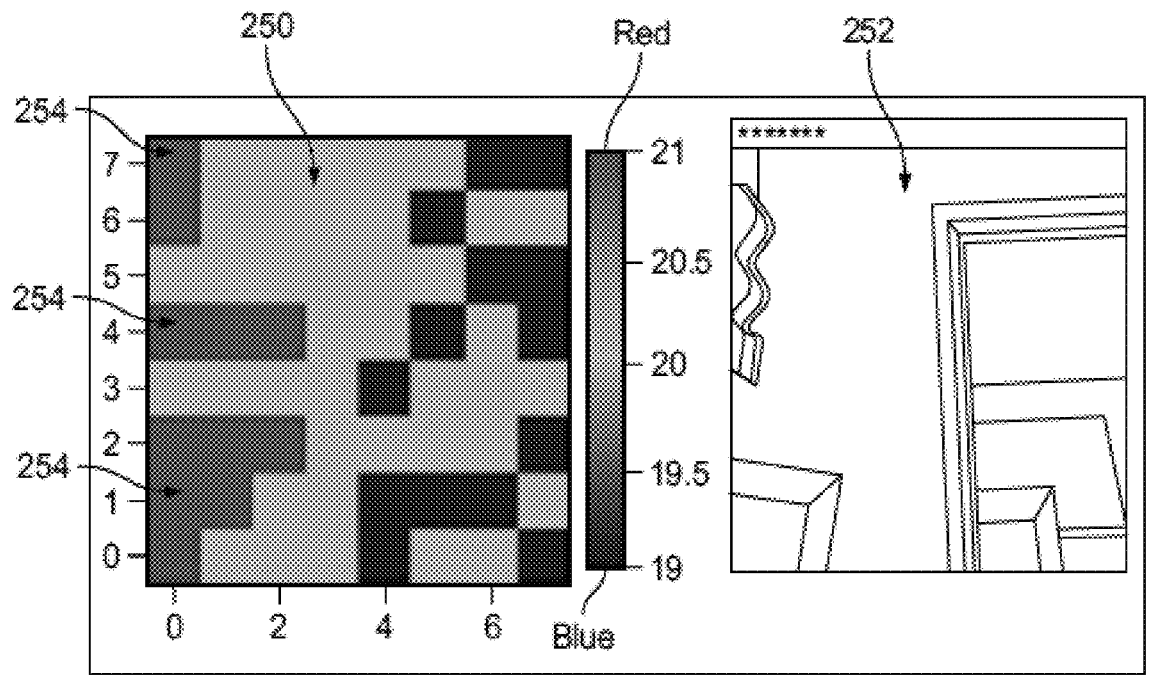
FIG. 7A shows an example thermal image captured by at least one sensor of the mobile robot where no human and/or animal is present according to an implementation of the disclosed subject matter.

As discussed above, operations 16, 18, and/or 20 may use sensors, 102, 106 to determine whether a human and/or animal is present within the area. FIG. 7A shows an example thermal image 250 that may be captured by at least one sensor 102, 106 of the mobile robot 100 where no human and/or animal is present according to an implementation of the disclosed subject matter. Image 252 may be a camera image captured by the at least one sensor 102, 106, which shows that no human and/or animal is present. Although the thermal image 250 includes areas 254 of high thermal energy, the shape of areas 254 may be determined by controller 114 (shown in FIG. 10), and/or server 140 and/or remote platform 160 of FIG. 11 as being non-human, based on the pattern of areas 254. The image 252 may be used to confirm that a human and/or an animal is not present in the thermal image 250.

Figure 7B:
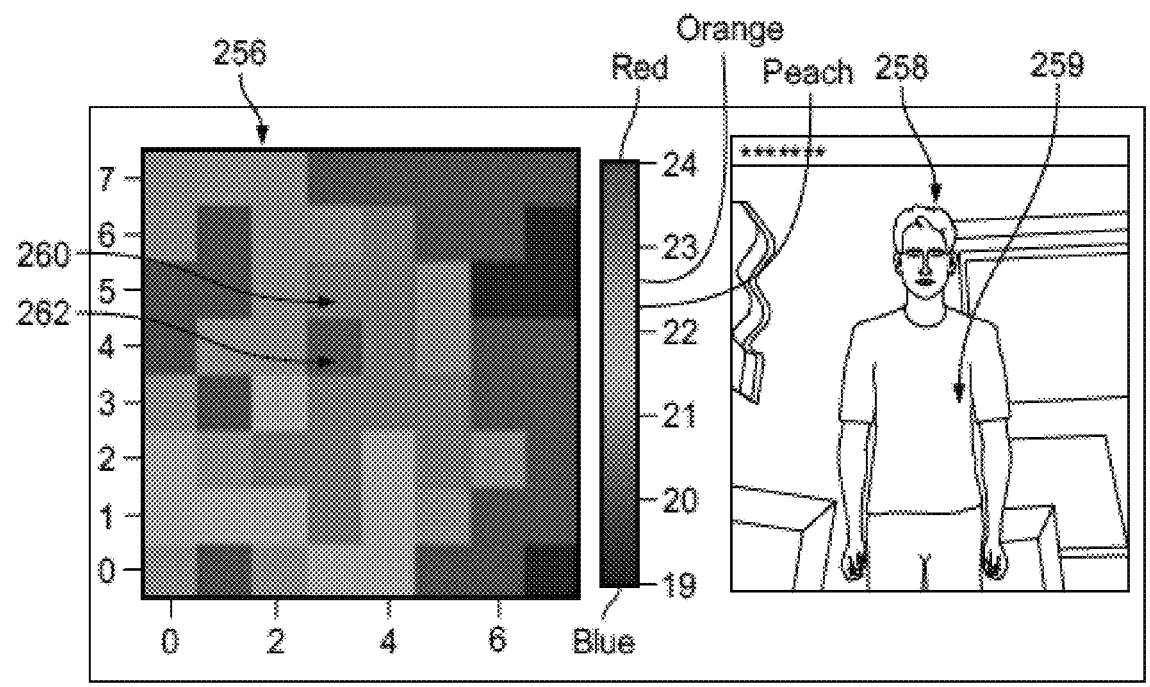
FIG. 7B shows an example thermal image captured by at least one sensor of the mobile robot where a human and/or an animal is present according to an implementation of the disclosed subject matter.

FIG. 7B shows an example thermal image 256 captured by at least one sensor 102, 106 of the mobile robot where a human 259 is present according to an implementation of the disclosed subject matter. Image 258 may be a camera image captured by the at least one sensor 102, 106, which shows that the human 259 is present. The thermal image 256 may include areas 260 and 262 which may have thermal energy levels greater than a predetermined amount that are in a shape of a human as determined by controller 114 (shown in FIG. 10), and/or server 140 and/or remote platform 160 of FIG. 11. The pattern of areas 254 may be confirmed to be human based on the image 258.

Figure 7C:
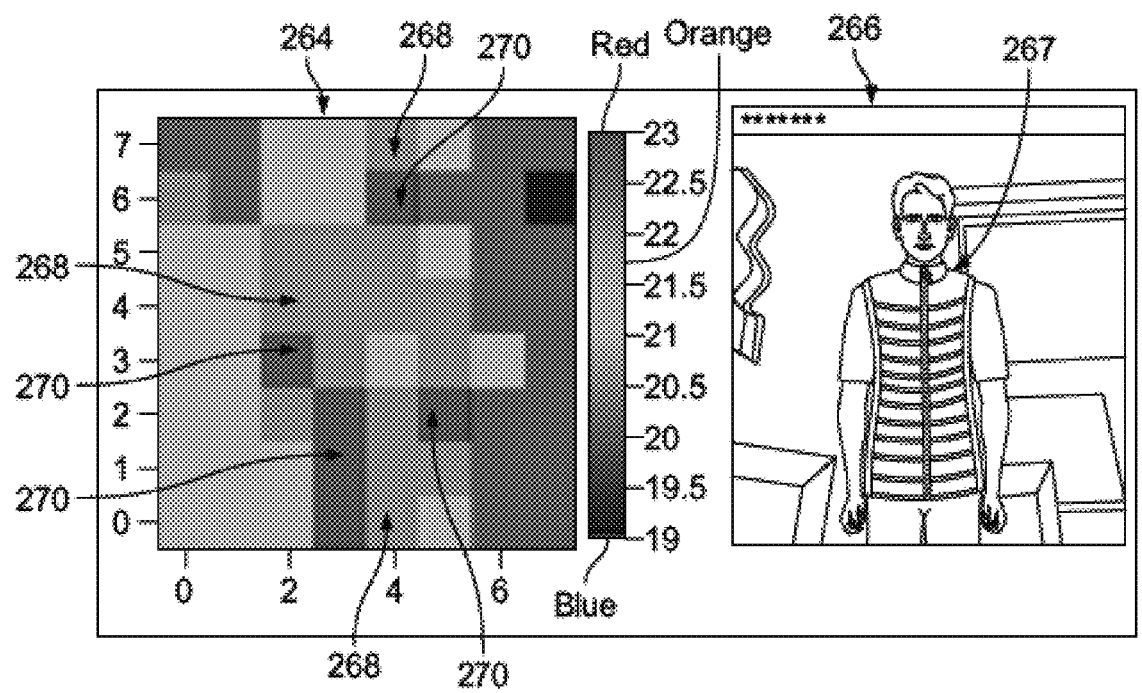
FIG. 7C shows an example thermal image captured by at least one sensor of the mobile robot where the human and/or animal detected in FIG. 7B is present with different clothing according to an implementation of the disclosed subject matter.

FIG. 7C shows an example thermal image 264 captured by at least one sensor 102, 106 of the mobile robot where the human detected in FIG. 7B is present with different clothing (e.g., human 267) according to an implementation of the disclosed subject matter. Image 266 may be a camera image captured by the at least one sensor 102, 106, which shows that the human 267 is present, with different clothing from human 259 shown in FIG. 7B. The thermal image 264 may include areas 268 and 270 which may have thermal energy levels greater than a predetermined amount that are in a shape of a human, as determined by controller 114 (shown in FIG. 10), and/or server 140 and/or remote platform 160 of FIG. 11 as being non-human, based on the pattern of areas 254. The shape of the areas 268 and 270 may be different from that of areas 260 and 262 of FIG. 7B, but may be identified as being a human shape, which may be verified using, for example, image 266.

That is, a controller (e.g., controller 114 shown in FIG. 10, and/or server 140 and/or remote platform 160 shown in FIG. 11) and/or the sensor 102, 106 may perform human and/or animal detection based on signals received from the one or more sensor (e.g., the thermal camera, the RGB camera, and the like). For example, if the detected shape of the object resembles a human and/or an animal, the object may be determined to be a human and/or an animal.

In some implementations, motion in the area may be initially determined by the sensor 102, 106 as being a human and/or an animal. Although the motion may not necessarily be a human and/or an animal, when the determination that the motion is from a human and/or an animal, the mobile robot may stop the output of UV light by the light source to prevent harm to any human and/or animal, and use the sensors 102, 106 and/or microphone 103 over a predetermined period of time to more accurately determine whether the human and/or animal is within the area.

In some implementations, humans and/or animals may be detected within the area by using YOLO (You Only Look Once), a single neural network is applied to a full image. The network divides the image into regions, and predicts bounding boxes and probabilities for each region. These bounding boxes may be weighted by the predicted probabilities. YOLO has several advantages over typical classifier-based systems. YOLO may use the whole image at test time, so its predictions may be based on the global context in the image. Yolo may also make predictions with a single network evaluation, unlike other systems which require thousands for a single image.

In some implementations, humans and/or animals may be detected using SSD (Single Shot Multibox Detection), which is a method for detecting objects in images using a single deep neural network. SSD may discretize the output space of bounding boxes into a set of default boxes over different aspect ratios and scales per feature map location. At prediction time, the network may generate scores for the presence of each object category in each default box, and may produce adjustments to the box to better match the object shape. The network may combine predictions from multiple feature maps with different resolutions to naturally handle objects of various sizes. SSD may be simple relative to traditional methods that require object proposals, as SSD eliminates proposal generation and subsequent pixel or feature resampling stage and encapsulates all computation in a single network. SSD may be easier to train and may have better accuracy than single stage method, even with a smaller input image size.

The YOLO, SSD, and other human and/or animal detection methods may be used, for example, when the mobile robot is in a static position (i.e., not moving) the mobile robot is static.

In some implementations, humans and/or animal may be detected in the by the mobile robot based on sound received by the microphone (e.g., microphone 103 shown in FIGS. 4-6, 8, and 10). For example, Voice Activity Detection (VAD) may be used (e.g., by the controller 114 shown in FIG. 10, and/or the server 140 and/or the remote platform 160 shown in FIG. 11). VAD may be used determine if speech and/or noise from a human and/or animal is present or not in the area, even when there is background noise. VAD may break an audio signal (e.g., as received by the microphone 103) into frames, extract features from each frame, train a classifier on a known set of speech and silence frames, and classify unseen frames as speech or silence.

Implementations of the disclosed subject matter may combine two or more of the methods disclosed above (e.g., thermal imaging, YOLO, SSD, VAD, and the like) to increase the robustness of the system. For example, to prevent a human and/or an animal from being harmed by the output of UV light, the mobile robot may be stopped and the output of UV light may be stopped if motion is initially detected. The mobile robot may use the sensors 102, 106 and/or microphone 103 for a predetermined period of time to determine if a human and/or an animal is within the area. If a human and/or animal is not detected within the predetermined time, the mobile robot may output UV light and continue to disinfect the area. If a human and/or an animal is detected, the mobile robot may output a notification and/or instructions requesting that the human and/or animal leave the area so that disinfection may resume.

In some implementations, such as at operation 22 shown in FIG. 1, when the at least one sensor determines that there is no human and/or animal identification, motion, heat, and/or sound within the predetermined period of time, the light source may be controlled to emit UV light and the drive system to move the mobile robot within the area. For example, the controller 114 shown in FIG. 10 may control the light source 104 and/or the drive system 108 of the mobile robot to move about path 306 in area 300 shown in FIG. 9 to disinfect the area, including beds 312, sink 308, 4-hook IV stands 314, and the like while there are no humans and/or animals present in the area.

At operation 24 shown in FIG. 1, when the at least one sensor determines that there is at least one of human and/or animal identification, motion, heat, and/or sound within the predetermined period of time, the light source may be controlled to prohibit the emission of UV light. For example, the controller 114 shown in FIG. 10 may control the light source 104 to prohibit the emission of UV light.

In some implementations, a notification may be output that the human and/or animal is determined to be in the area, the movement of the mobile robot is being stopped, and/or the emission of the UV light from the light source is stopped. The output notification may be an audible notification and/or a visual notification. For example, the speaker 107 (shown in FIG. 10) of the mobile robot 100 may output the audible notification that the human and/or animal is determined to be in the area, the movement of the mobile robot is being stopped, and/or the emission of the UV light from the light source is stopped. The user interface 110 (shown in FIG. 10) of the mobile robot 100 may include a display to display the visual notification that the human and/or animal is determined to be in the area, the movement of the mobile robot is being stopped, and/or the emission of the UV light from the light source is stopped.

In some implementations, the notification may be transmitted using a communications interface of the mobile robot via a communications network. For example, the notification may be transmitted using the network interface 116 (shown in FIG. 10) of the mobile robot 100 via the network 130 to the server 140, database 150, and/or remote platform 160 shown in FIG. 11.

In some implementations, the location of the detected human as a non-human and/or the location of the detected animal as a non-animal on a map of the area in a memory that is communicatively coupled to the controller based on a signal received by a communications interface of the mobile robot via a communications network or an input received from an interface of the mobile robot. For example, operation 16 may determine that there is a human and/or an animal present in the area, but operation 20 may determine that there is no human and/or animal (i.e., the object originally detected is human is non-human, and/or the object originally detected as an animal is non-animal) in the area based on the lack of a human and/or animal identification, motion detection, the heat, and/or sound signals generated by the at least one sensor. The location of the non-human and/or non-animal in the area may be stored in the fixed storage 120 (shown in FIG. 10) and/or the memory 118 of the mobile robot 100, and/or at the server 140, database 150, and/or remote platform 160 as shown in FIG. 11. The location of the non-human and/or non-animal may be determined by at least one of the sensor 102 and/or 106 of the mobile robot 100.

Figure 2:
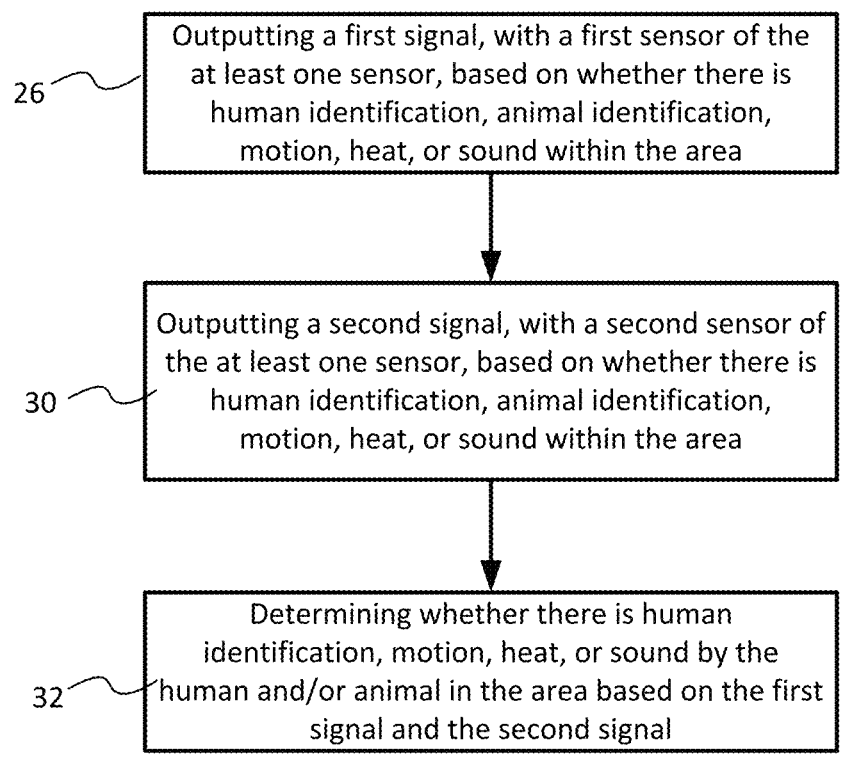
FIG. 2 shows that the example method of FIG. 1 may include determining when the human and/or animal is present in the area according to an implementation of the disclosed subject matter.

FIG. 2 shows example operations in connection with the operation 20 (shown in FIG. 1) of determining when the human and/or animal is present in the area according to an implementation of the disclosed subject matter. That is, the determining whether there is at least one human and/or animal identification, motion, heat, and/or sound within the area may include operation 26, where a first signal may be output with a first sensor of the at least one sensor, based on whether there is human and/or animal identification, motion, heat, and/or sound within the area. For example, sensor 102, sensor 102, and/or microphone 109 may output a signal that may be used (e.g., by controller 114 shown in FIG. 10 and/or server 140 and/or remote platform 160 shown in FIG. 11) to determine whether there is human and/or animal identification, motion, heat, and/or sound within the area. The sensor 102, 106 may capture an image of a human and/or animal in the area, may detect motion within the area, and/or may detect heat within the area and may output a signal. The microphone 109 may output a signal if there is noise within the area.

At operation 30, a second signal may be output with a second sensor of the at least one sensor, based on whether there is human and/or animal identification, motion, heat, or sound within the area. Similar to operation 28, at least one of sensor 102, sensor 102, and/or microphone 109 may output a signal that may be used (e.g., by controller 114 shown in FIG. 11 and/or server 140 and/or remote platform 160 shown in FIG. 12) to determine whether there is human and/or animal identification, motion, heat, and/or sound within the area.

At operation 32, the controller 114 shown in FIG. 10 and/or server 140 and/or remote platform 160 shown in FIG. 11 may determine whether there is human and/or animal identification, motion, heat, and/or sound by the human and/or animal in the area based on the first signal and the second signal. That is, the first signal and second signal may be used to verify whether a human and/or an animal has been detected by the sensor 102, sensor 106, and/or microphone 109. For example, if neither the first signal nor the second signal indicate that a human and/or an animal is present in the area, operation 32 may determine that a human and/or an animal is not present within the area. If only one of the first signal and the second signal indicate that a human and/or an animal is present in the area, operation 32 may determine that the human and/or an animal is not present. As a human and/or an animal is not present within the area, mobile robot may resume movement and outputting UV light to disinfect the area. In some implementations, if only one of the first signal and second signal indicate that the human and/or animal is present, the controller 114 may control the light source to prohibit the emission of UV light in order to increase safety. When both the first signal and the second signal indicate that a human and/or an animal is present in the area, the controller 114 may control the light source to prohibit the emission of UV light.

Figure 3:
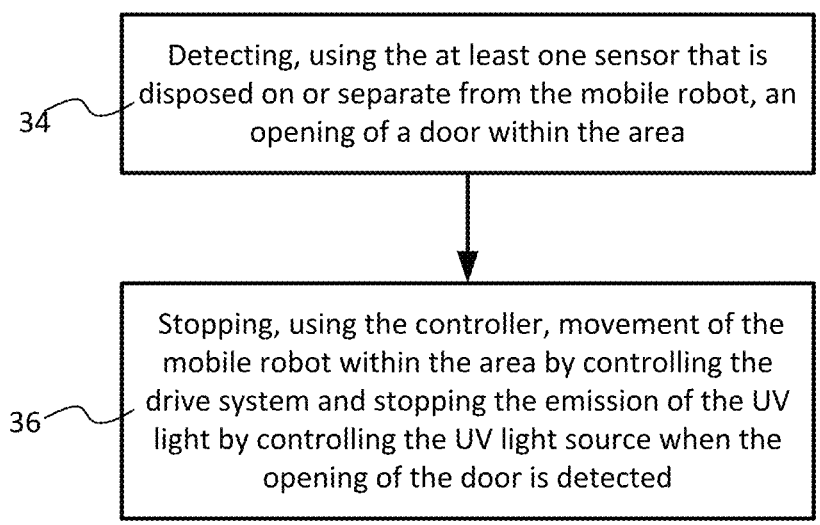
FIG. 3 shows that the example method of FIG. 1 may include a method of detecting a door opening within the area and stopping the movement and the UV light output by the robot based on the detection according to an implementation of the disclosed subject matter.

FIG. 3 shows the example method 10 of FIG. 1 may include a method of detecting a door opening within the area and stopping the movement and the UV light output by the robot based on the detection according to an implementation of the disclosed subject matter. At operation 34, an opening of a door within the area may be detected using the at least one sensor that is disposed on or separate from the mobile robot. For example, the sensor 102, 106 and/or the microphone 109 of the mobile robot 100 may be used to detect the opening of a door within the area. Sensor 304 may be separate from the mobile robot and may be used to detect the opening of the door 302 as shown in FIG. 8. Sensor 304 may be an infrared sensor, a passive infrared sensor (PIR), a motion sensor, or the like that may detect the motion of the door 302. Sensor 302 may be communicatively coupled to the mobile robot 100 via the network interface 116 and communications network 130. The sensor 304 may transmit a signal to the mobile robot when the door movement is detected (i.e., the door is being opened). At operation 36, the controller (e.g., controller 114) may stop the movement of the mobile robot within the area by controlling the drive system (e.g., drive system 108) and stopping the emission of the UV light by controlling the UV light source when the opening of the door is detected.

Figure 4:
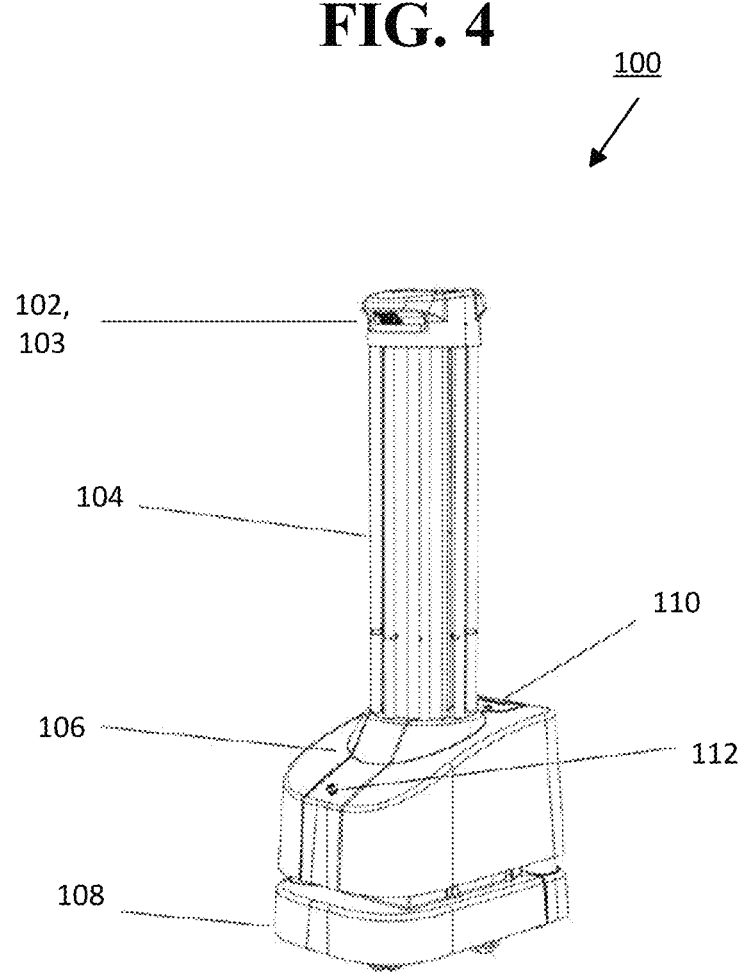
FIGS. 4-6 show a plurality of external views of the mobile robot having sensors and a light source to output UV light according to implementations of the disclosed subject matter.
Figure 5:
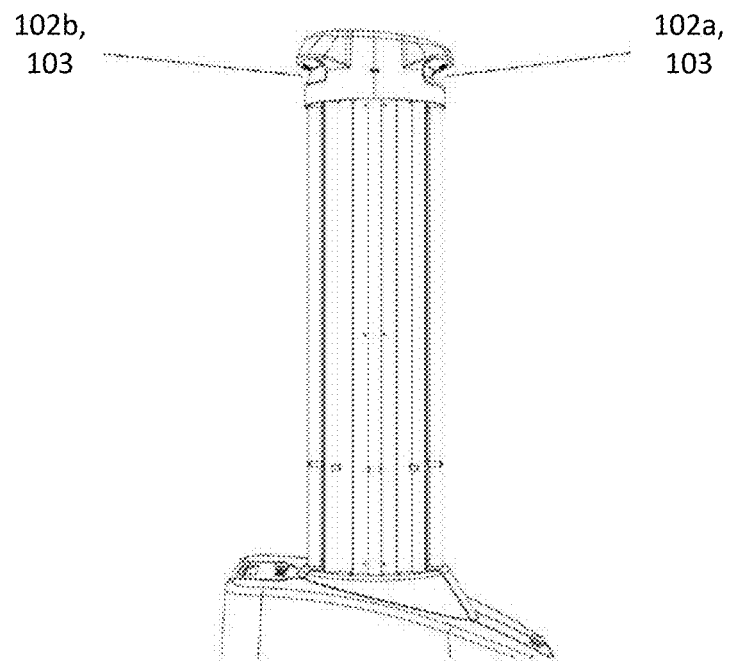
Figure 6:
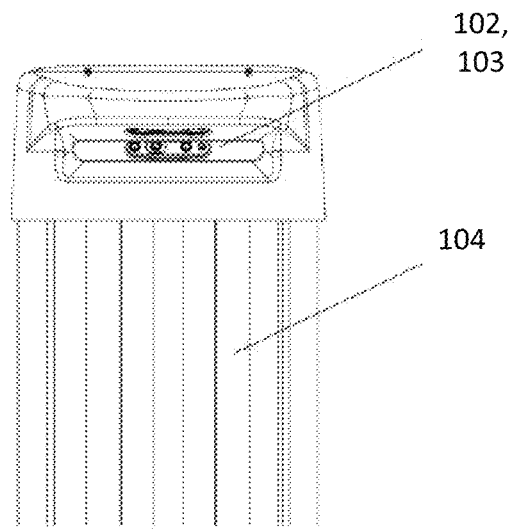

FIGS. 4-6 show a plurality of external views of a mobile robot 100 that includes sensors that may be used to detect humans and/or animals within the area and/or detect surfaces and objects in the area, and a light source to output UV light to disinfect the air, objects, and/or surfaces in the area according to implementations of the disclosed subject matter. The mobile robot 100 may include at least one sensor 102, 106 (where sensor 102 may be shown as sensor 102*a* and 102*b* in FIG. 5), a light source 104 to output ultraviolet light, a drive system 108, a user interface 110, and/or a stop button 112. A controller (e.g., controller 114 shown in FIG. 12 and described below) may be communicatively coupled to the at least one sensor 102 (and/or sensor 106), the light source 104, the drive system 108, the user interface 110 and the stop button 112, may control the operations of the mobile robot 100.

The at least one sensor 102 (including sensors 102*a*, 102*b* shown in FIG. 5) may determine whether a human and/or an animal is within the area, an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of a surface and/or object in the area. In some implementations, the first sensor 102 may detect air, a surface, and/or objects that may disinfected with UV light from the light source 104.

In some implementations, the at least one first sensor 102 may have a field of view of 70 degrees diagonally. The at least one sensor 102 may have a detection distance of 0.2-4 meters. As shown in FIGS. 4-6, the at least one first sensor 102 may be disposed over the light source 104.

The at least one first sensor 102 may include a first side sensor disposed on a first side of the mobile robot 100 and a second side sensor that may be disposed on a second side of the device. For example, as shown in FIG. 5, sensor 102*a* may be disposed on a first side (e.g., a front side) of the mobile robot 100, and sensor 102*b* may be disposed on a second side (e.g., a back side) of the mobile robot 100. Although sensors on two sides of the robot are shown in FIG. 6, there may be a plurality of sensors disposed on different sides of the mobile robot 102 to at least detect humans, animals, surfaces, and/or objects. In some implementations, sensor 102*a* and/or sensor 102*b* may be disposed over the light source 104.

The light source 104 may be one or more bulbs, one or more lamps, and/or an array of light emitting diodes (LEDs) or organic light emitting diodes (OLEDs) to emit UV light (e.g., light having a wavelength of 10 nm-400 nm). The dosage of the UV light (e.g., intensity, duration, optical power output, or the like) may be controlled by the controller 114, which may also turn on or off a portion or all of the devices (e.g., bulbs, lamps, LEDs, OLEDs) of the light source 104, for example, when a human and/or an animal is detected. The light source may be controlled to emit UV light when the mobile robot is within an area, and may be controlled to stop emitting light when a human and/or an animal is detected.

The at least one sensor 106 may be communicatively coupled to the controller 114 shown in FIG. 10, and may be used to detect whether a human and/or an animal is within the area. The sensor 106 may detect air, surfaces, and/or objects that may be mapped and/or disinfected with UV light from the light source 104. In some implementations, the at least one sensor 106 may determine at least one of an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of a surface and/or object in the area.

In some implementations, the sensor 102, 106 may be a time-of-flight sensor, an ultrasonic sensor, a two-dimensional (2D) Light Detection and Ranging (LiDAR) sensor, a three-dimensional (3D) LiDAR sensor, and/or a radar (radio detection and ranging) sensor, a stereo vision sensor, 3D camera, an image sensor, RGB (red green blue) camera, thermal camera, geometrical sensors, a microphone, a structured light camera, or the like. The sensor 106 may have a field of view of 20-27 degrees. In some implementations, the sensor 106 may have a detection distance of 0.05-4 meters.

The mobile robot 100 may include a motor to drive the drive system 108 to move the mobile robot in an area, such as a room, a building, or the like. The drive system 108 may include wheels, which may be adjustable so that the drive system 108 may control the direction of the mobile robot 100.

In some implementations, the mobile robot 100 may include a base with the drive system 108, and the sensor 102, 106 may be disposed on the base.

The controller 114 may control and/or operate the mobile robot 100 in an operation mode which may be a manual mode, an autonomous mode, and/or a tele-operation mode. In the manual mode, the controller 114 may receive on or more control signals from the user interface 110 and/or the stop button 112. For example, a user may control the movement, direction, and/or stop the motion of the mobile robot 100 (e.g., when a human and/or an animal is detected in the area) by making one or more selections on the user interface 110. The stop button 112 may be an emergency stop (ESTOP) button which may stop all operations and/or movement of the mobile robot 100 when selected. In some implementations, the controller 114 may receive at least one control signal via a network interface 116 (shown in FIG. 10) when operating when operating in the tele-operation mode. For example, the network interface may receive control signals via network 130 from server 140, database 150, and/or remote platform 160, as described below in connection with FIG. 11.

In some implementations, when the mobile robot 100 is moving in a direction, the sensor 102, 106 may detect a geometry of a human, an animal, one or more surfaces, objects, or the like. The output of the sensor 102, 106 may be, for example, a point cloud of a human, an animal, and/or the one or more objects in the path of the mobile robot 100. When the sensor 102 and/or sensor 106 is a stereo vision sensor, images from two sensors (i.e., where the two sensors may be part of the stereo vision sensor of the sensor 102 and/or sensor 106) within a known distance from one another distance may be captured at a predetermined point in time, and/or at predetermined time intervals with a global shutter. The global shutter may be configured so that the two sensors of the stereo vision sensor may capture images about simultaneously. One or more features may be determined from the captured images, and be compared to one another to determine portions that are matching. As the focal length of the two sensors of the stereo vision sensor and the distance between the two sensors (e.g., about 6 cm) may be stored in memory 118 and/or fixed storage 120 (shown in FIG. 10), the controller 114 and/or the at least one first sensor 102 may use the captured images and the stored values to determine the distance from the sensor 102, 106 to the surfaces and/or objects, and may be used by the processor for outputting a dosage of UV light from the light source. In some implementations, the sensor 102, 106 may include at least one laser, LED, and/or OLED, to radiate one or more points on surfaces of objects, when the objects may be without identifying features (e.g., blank walls).

When detecting a human, an animal, a surface, and/or an object, the sensor 102, 106 may be a time-of-flight (TOF) sensor. At least one photon of light may be output by the sensor 102, 106, and may be transmitted through the air. When the at least one photon of light radiates the human, animal, surface, and/or object, a portion of the light may be reflected by the human, animal, surface, and/or the object may return to a receiver portion of the sensor 102, 106. The sensor 106 may calculate the time between sending the at least one photon of light and receiving the reflection, and multiply this value by the speed of light in air, to determine the distance between the sensor 102, 106 and a human, animal, surface, and/or object. This may be used to determine whether a human and/or an animal is in the area, and/or generate the map of the area that the mobile robot is operating within.

FIG. 10 shows example components of the mobile robot 100 suitable for providing the implementations of the disclosed subject matter. The mobile robot 100 may include a bus 122 which interconnects major components of the mobile robot 100, such as the drive system 108, a network interface 116 operable to communicate with one or more remote devices via a suitable network connection, the controller 114, a memory 118 such as Random Access Memory (RAM), Read Only Memory (ROM), flash RAM, or the like, the stop button 112, the light source 104, the at least one first sensor 102, a user interface 110 that may include one or more controllers and associated user input devices such as a keyboard, touch screen, and the like, a fixed storage 120 such as a hard drive, flash storage, and the like, the at least one second sensor 106, a microphone 103, and a speaker 107 to output an audio notification and/or other information.

The bus 122 allows data communication between the controller 114 and one or more memory components, which may include RAM, ROM, and other memory, as previously noted. Typically RAM is the main memory into which an operating system and application programs are loaded. A ROM or flash memory component can contain, among other code, the Basic Input-Output system (BIOS) which controls basic hardware operation such as the interaction with peripheral components. Applications resident with the mobile robot 100 are generally stored on and accessed via a computer readable medium (e.g., fixed storage 120), such as a solid state drive, hard disk drive, an optical drive, solid state drive, or other storage medium.

The network interface 116 may provide a direct connection to a remote server (e.g., server 140, database 150, and/or remote platform 160 shown in FIG. 13) via a wired or wireless connection (e.g., network 130 shown in FIG. 13). The network interface 116 may provide such connection using any suitable technique and protocol as will be readily understood by one of skill in the art, including digital cellular telephone, WiFi, Bluetooth®, near-field, and the like. For example, the network interface 116 may allow the mobile robot 100 to communicate with other computers via one or more local, wide-area, or other communication networks, as described in further detail below. The mobile robot may transmit data via the network interface to the remote server that may include whether a human and/or an animal is detected, a path of operation, the surfaces and/or areas radiated with UV light, and the like.

Many other devices or components (not shown) may be connected in a similar manner. Conversely, all of the components shown in FIG. 10 need not be present to practice the present disclosure. The components can be interconnected in different ways from that shown. Code to implement the present disclosure can be stored in computer-readable storage media such as one or more of the memory 118, fixed storage 120, or on a remote storage location.

FIG. 11 shows an example network arrangement according to an implementation of the disclosed subject matter. Mobile robot 100 described above, and/or a similar mobile robot 200 may connect to other devices via network 130. The network 130 may be a local network, wide-area network, the Internet, or any other suitable communication network or networks, and may be implemented on any suitable platform including wired and/or wireless networks. The mobile robot 100 and/or mobile robot 200 may communicate with one another, and/or may communicate with one or more remote devices, such as server 140, database 150, and/or remote platform 160. The remote devices may be directly accessible by the mobile robot 100, 200 or one or more other devices may provide intermediary access such as where a server 140 provides access to resources stored in a database 150. The mobile robot 100, 200 may access remote platform 160 or services provided by remote platform 160 such as cloud computing arrangements and services. The remote platform 160 may include one or more servers 140 and/or databases 150.

More generally, various implementations of the presently disclosed subject matter may include or be embodied in the form of computer-implemented processes and apparatuses for practicing those processes. Implementations also may be embodied in the form of a computer program product having computer program code containing instructions embodied in non-transitory and/or tangible media, such as solid state drives, DVDs, CD-ROMs, hard drives, USB (universal serial bus) drives, or any other machine readable storage medium, such that when the computer program code is loaded into and executed by a computer, the computer becomes an apparatus for practicing implementations of the disclosed subject matter. Implementations also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing implementations of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Implementations may include using hardware that has a processor, such as a general purpose microprocessor and/or an Application Specific Integrated Circuit (ASIC) that embodies all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A method comprising:
   moving, using a drive system, a mobile robot within an area;
   emitting, using a light source of the mobile robot, ultraviolet (UV) light to disinfect at least a portion of the area;

while emitting the UV light, determining whether there is at least one of the group consisting of: a human, and an animal within the area using at least one sensor;

stopping, using a controller, movement of the mobile robot within the area by controlling the drive system and stopping the emission of the UV light by controlling the UV light source when the at least one of the human and the animal is determined to be within the area;

determining, using the at least one sensor, whether there is at least one selected from the group consisting of: human identification, animal identification, motion, heat, and sound within the area for a predetermined period of time;

storing at least one of the location of the detected human as a non-human and the location of the detected animal as a non-animal on a map of the area in a memory that is communicatively coupled to the controller based on a signal received by a communications interface of the mobile robot via a communications network or an input received from an interface of the mobile robot;

when the at least one sensor determines that there is no human identification, animal identification, motion, heat, and sound within the predetermined period of time, controlling the light source to emit UV light and controlling the drive system to move the mobile robot within the area; and when the at least one sensor determines that there is at least one of the group consisting of: human identification, animal identification, motion, heat, and sound within the predetermined period of time, controlling the light source to prohibit the emission of UV light.

2. The method of claim 1, further comprising:
outputting a notification that the at least one of the human and the animal is determined to be in the area, the movement of the mobile robot is being stopped, and the emission of the UV light from the light source is stopped.

3. The method of claim 2, wherein the outputting the notification comprises: outputting the notification selected from at least one of the group consisting of: an audible notification, and a visual notification.

4. The method of claim 2, wherein the outputting comprises:
transmitting, using a communications interface, the notification via a communications network.

5. The method of claim 1, wherein the determining whether the human is within the area comprises:
capturing an image, using at least one sensor, to determine whether the at least one of the human and the animal is within the area.

6. The method of claim 1, wherein the determining whether the at least one of the human and the animal is within the area comprises:
capturing a thermal image, using a thermal sensor of the at least one sensor, to determine whether the at least one of the human and the animal is within the area.

7. The method of claim 1, wherein the determining whether there is at least one selected from the group consisting of: human identification, animal identification, motion, heat, and sound within the area further comprises:
outputting a first signal, with a first sensor of the at least one sensor, based on whether there is human identification, animal identification, motion, heat, or sound within the area;
outputting a second signal, with a second sensor of the at least one sensor, based on whether there is human identification, animal identification, motion, heat, or sound within the area; and
determining whether there is human identification, animal identification, motion, heat, or sound by the at least one of the human and the animal in the area based on the first signal and the second signal.

8. The method of claim 1, further comprising:
detecting, using the at least one sensor that is disposed on or separate from the mobile robot, an opening of a door within the area; and
stopping, using the controller, movement of the mobile robot within the area by controlling the drive system and stopping the emission of the UV light by controlling the UV light source when the opening of the door is detected.

\* \* \* \* \*